(12) United States Patent
Hauck et al.

(10) Patent No.: US 6,996,264 B2
(45) Date of Patent: Feb. 7, 2006

(54) INDENTATION HARDNESS TEST SYSTEM

(75) Inventors: John Michael Hauck, Bridgman, MI (US); David Andrew Barfoot, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 123 days.

(21) Appl. No.: 10/679,823

(22) Filed: Oct. 6, 2003

(65) Prior Publication Data

US 2004/0096093 A1 May 20, 2004

Related U.S. Application Data

(60) Provisional application No. 60/419,475, filed on Oct. 18, 2002.

(51) Int. Cl.
*G06K 9/00* (2006.01)

(52) U.S. Cl. ...................................... 382/141; 382/199

(58) Field of Classification Search ................ 382/108, 382/141, 152, 199, 284, 286; 73/78, 81
See application file for complete search history.

(56) References Cited

U.S. PATENT DOCUMENTS

| | | | |
|---|---|---|---|
| 4,589,140 A | 5/1986 | Bishop et al. | |
| 4,618,938 A | 10/1986 | Sandland et al. | |
| 4,757,550 A | 7/1988 | Uga | |
| 4,764,969 A | 8/1988 | Ohtombe et al. | |
| 4,825,388 A | 4/1989 | Dailey et al. | |
| 4,945,490 A * | 7/1990 | Biddle et al. ................. | 702/33 |
| 5,022,089 A | 6/1991 | Wilson | |
| 5,146,779 A | 9/1992 | Sugimoto et al. | |
| 5,264,919 A | 11/1993 | tsukada | |
| 5,486,924 A | 1/1996 | Lacey | |
| 5,513,275 A | 4/1996 | Khalaj et al. | |
| 5,517,235 A | 5/1996 | Wasserman | |
| 5,586,058 A | 12/1996 | Aloni et al. | |
| 5,592,563 A | 1/1997 | Zahavi | |
| 5,619,429 A | 4/1997 | Aloni et al. | |
| 5,717,780 A | 2/1998 | Mitsumune et al. | |
| 5,768,401 A | 6/1998 | Csipkes et al. | |
| 5,796,861 A | 8/1998 | Vogt et al. | |
| 5,949,389 A | 9/1999 | Brown | |
| 5,987,189 A | 11/1999 | Schmucker et al. | |
| 5,991,461 A | 11/1999 | Schmucker et al. | |
| 5,999,262 A | 12/1999 | Dobschal et al. | |

(Continued)

OTHER PUBLICATIONS

Mitutoyo Technical Data, Bulletin No. 1463, "Auto Vickers Hardness Testing System AAV–602," Mitutoyo American Corporation, Aurora, Illinois, Oct. 2000 (2 pages).
U.S. Patent Application Publication No. 2002/0128913, Sep. 12, 2002, Kotake et al.
U.S. Patent Application Publication No. 2002/0047895, Apr. 25, 2002, Bernardo et al.
U.S. Patent Application Publication No. 2002/0034338, Mar. 21, 2002, Askery.

*Primary Examiner*—Phuoc Tran
(74) *Attorney, Agent, or Firm*—Price, Heneveld, Cooper, DeWitt & Litton, LLP

(57) ABSTRACT

An indentation hardness test system includes a frame having a movable turret, a movable stage for receiving a part, a camera, a display, a processor and a memory subsystem. The turret includes an objective lens of a microscope and an indenter and the movable stage is configured for receiving the part to be tested. The camera captures images of the part through the microscope, which can then be provided on the display. The processor is coupled to the turret, the movable stage, the camera and the display, as well as the memory subsystem. The memory subsystem stores executable code that instructs the processor to capture and store a series of real-time images of the part using the camera, store associated stage coordinates provided by the stage for the images and display a composite image, which includes the series of real-time images assembled according to the associated stage coordinates, of the part.

23 Claims, 10 Drawing Sheets

U.S. PATENT DOCUMENTS

| | | |
|---|---|---|
| 6,031,930 A | 2/2000 | Bacus et al. |
| 6,078,681 A | 6/2000 | Silver |
| 6,101,265 A | 8/2000 | Bacus et al. |
| 6,144,028 A | 11/2000 | Kley |
| 6,201,899 B1 | 3/2001 | Bergen |
| 6,219,437 B1 | 4/2001 | Baldur |
| 6,226,392 B1 | 5/2001 | Bacus et al. |
| 6,268,611 B1 | 7/2001 | Pettersson et al. |
| 6,272,235 B1 | 8/2001 | Bacus et al. |
| 6,345,129 B1 | 2/2002 | Aharon |
| 6,347,150 B1 | 2/2002 | Hiroi et al. |
| 6,360,005 B1 | 3/2002 | Aloni et al. |
| 6,362,832 B1 | 3/2002 | Stephan et al. |
| 6,587,597 B1 | 7/2003 | Nakao et al. |
| 6,731,390 B2 | 5/2004 | Schoeppe |
| 2001/0030654 A1 | 10/2001 | Ikl |
| 2002/0036775 A1 | 3/2002 | Wolleschensky et al. |
| 2003/0231408 A1 | 12/2003 | Wolleschensky |
| 2004/0095576 A1 | 5/2004 | Wolleschensky |
| 2004/0159797 A1 | 8/2004 | Wolleschensky |

\* cited by examiner

PRIOR ART

INDENTATION HARDNESS TEST SYSTEM

This application claims the benefit of U.S. Provisional Patent Application Ser. No. 60/419,475, entitled "MICRO HARDNESS TEST SYSTEM," which was filed Oct. 18, 2002, and which is hereby incorporated herein by reference in its entirety.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

REFERENCE TO COMPUTER PROGRAM LISTING APPENDIX

A computer program listing appendix on one compact disc (labeled "Computer Program Listing Appendix—Disc 1/Copy 1") includes the following files:

| File Name | Creation Date | Size (bytes) |
|---|---|---|
| BasicDrawing.cpp | Oct. 1, 2003 | 1,766 |
| BasicDrawing.h | Oct. 1, 2003 | 1,310 |
| BasicHandle.cpp | Oct. 1, 2003 | 5,194 |
| BasicHandle.h | Oct. 1, 2003 | 3,005 |
| BasicNavigationPoint.cpp | Oct. 1, 2003 | 2,077 |
| BasicNavigationPoint.h | Oct. 1, 2003 | 1,260 |
| CompositeImage.cpp | Oct. 1, 2003 | 23,476 |
| CompositeImage.h | Oct. 1, 2003 | 1,935 |
| CompositeImaging.h | Oct. 1, 2003 | 714 |
| CompositeLiveOverlay.cpp | Oct. 1, 2003 | 8,958 |
| CompositeLiveOverlay.h | Oct. 1, 2003 | 1,590 |
| CompositeStageMediator.cpp | Oct. 1, 2003 | 5,174 |
| CompositeStageMediator.h | Oct. 1, 2003 | 982 |
| CompositeViewLayer.cpp | Oct. 1, 2003 | 6,467 |
| CompositeViewLayer.h | Oct. 1, 2003 | 1,502 |
| Drawable.h | Oct. 1, 2003 | 392 |
| Drawing.h | Oct. 1, 2003 | 2,152 |
| DrawingTool.cpp | Oct. 1, 2003 | 1,390 |
| DrawingTool.h | Oct. 1, 2003 | 2,255 |
| DrawingView.h | Oct. 1, 2003 | 1,141 |
| Figure.cpp | Oct. 1, 2003 | 935 |
| Figure.h | Oct. 1, 2003 | 4,153 |
| FigureBase.cpp | Oct. 1, 2003 | 3,595 |
| FigureBase.h | Oct. 1, 2003 | 1,729 |
| Geometry.cpp | Oct. 2, 2003 | 11,490 |
| Geometry.h | Oct. 1, 2003 | 6,242 |
| Grabber.cpp | Oct. 1, 2003 | 14,952 |
| Grabber.h | Oct. 1, 2003 | 2,950 |
| GrabberProvider.h | Oct. 1, 2003 | 1,184 |
| GraphicPrimitives.cpp | Oct. 2, 2003 | 9,612 |
| GraphicPrimitives.h | Oct. 1, 2003 | 4,085 |
| IaDoc.cpp | Oct. 1, 2003 | 23,986 |
| IaDoc.h | Oct. 1, 2003 | 6,228 |
| Image.h | Jun. 10, 2003 | 3,201 |
| ImageOverlay.h | Jun. 10, 2003 | 1,916 |
| Indent.cpp | Oct. 1, 2003 | 49,537 |
| Indent.h | Oct. 1, 2003 | 10,349 |
| IndentDrawing.cpp | Oct. 1, 2003 | 40,163 |
| IndentDrawing.h | Oct. 1, 2003 | 7,182 |
| IndentGroup.cpp | Oct. 1, 2003 | 49,011 |
| IndentGroup.h | Oct. 1, 2003 | 9,937 |
| IndentPosLine.cpp | Oct. 1, 2003 | 14,448 |
| IndentPosLine.h | Oct. 1, 2003 | 3,325 |
| IndentVector.cpp | Oct. 1, 2003 | 19,455 |
| IndentVector.h | Oct. 1, 2003 | 4,190 |
| InImageSource.cpp | Oct. 1, 2003 | 10,883 |
| InImageSource.h | Oct. 1, 2003 | 1,806 |
| MoveInfoImpl.cpp | Oct. 1, 2003 | 1,807 |
| MoveInfoImpl.h | Oct. 1, 2003 | 1,203 |
| MtCamera.h | Oct. 1, 2003 | 1,578 |
| MtStage.cpp | Oct. 1, 2003 | 54,322 |
| MtStage.h | Oct. 1, 2003 | 15,851 |
| MtStageCom.cpp | Oct. 1, 2003 | 13,620 |
| MtStageCom.h | Oct. 1, 2003 | 2,094 |
| MtTrace.cpp | Jul. 22, 2003 | 21,219 |
| MtTrace.h | Jun. 10, 2003 | 3,314 |
| NavigationPoint.h | Oct. 1, 2003 | 1,818 |
| Objective.cpp | Jun. 10, 2003 | 7,464 |
| Objective.h | Jun. 10, 2003 | 2,481 |
| PanopticSettings.h | Oct. 1, 2003 | 713 |
| PanopticView.cpp | Oct. 1, 2003 | 43,831 |
| PanopticView.h | Oct. 1, 2003 | 5,994 |
| PatternPreferences.cpp | Oct. 1, 2003 | 3,542 |
| PatternPreferences.h | Oct. 1, 2003 | 2,946 |
| PositionTool.cpp | Oct. 1, 2003 | 10,992 |
| PositionTool.h | Oct. 1, 2003 | 1,465 |
| TextFigure.cpp | Oct. 2, 2003 | 6,380 |
| TextFigure.h | Oct. 2, 2003 | 2,929 |
| TransformationMatrix2D.cpp | Oct. 1, 2003 | 3,771 |
| TransformationMatrix2D.h | Oct. 1, 2003 | 1,915 |
| ViewLayer.h | Oct. 1, 2003 | 565 | and an identical copy (labeled "Computer Program Listing Appendix—Disc 1/Copy 2") of the compact disc (labeled "Computer Program Listing Appendix—Disc 1/Copy 1") are attached hereto. The files included on Disc 1/Copy 1 on CD-R are in ASCII file format. The above-referenced computer program listing provided on the compact disc labeled "Computer Program Listing Appendix—Disc 1/Copy 1" is hereby incorporated herein by reference in its entirety.

BACKGROUND OF THE INVENTION

The present invention is generally directed to a test system and, more specifically, to an indentation hardness test system.

Hardness testing has been found to be useful for material evaluation and quality control of manufacturing processes and research and development endeavors. The hardness of an object, although empirical in nature, can be correlated to tensile strength for many metals and provides an indicator of wear-resistance and ductility of a material. A typical indentation hardness tester utilizes a calibrated machine to force a diamond indenter (of a desired geometry) into the surface of a material being evaluated. The indentation dimension (dimensions) is (are) then measured with a light microscope after load removal. A determination of the hardness of the material under test may then be obtained by dividing the force applied to the indenter by the projected area of the permanent impression made by the indenter.

In a typical situation, an operator of an indentation hardness tester is required to position indents into a part at precise distances from various part geometries. With reference to FIGS. 2 and 3, an operator may be required to place a series of five evenly spaced indents 302 into a surface of a tooth 102A of a portion of, for example, a gear 102 being tested and mounted within a plastic 104 to form a test assembly 22. The indents 302 may be spaced 200 microns (±5 microns) from each other and centered in a face of the tooth 102A. Assuming that the tooth 102A is approximately 0.5 cm wide by 0.5 cm tall and the tester has two magnifications, i.e., a high power 50× objective with a field of view 200 microns wide and a 5× magnification with a field of view 2000 microns wide, and assuming that an image of the tooth 102A is displayed on a display having a width of 640 pixels, the width of each pixel is about 0.3 microns at 50× and about 3.0 microns at 5× magnification.

In such a tester, a 5× magnification only allows an operator to see about $\tfrac{1}{5}^{th}$ of the top surface of a tooth and a 50× magnification only allows the operator to see about 1/50th of the top surface of a tooth. It should be appreciated that such a view does not allow an operator to precisely know if a stage that is used to position the test assembly 22 is positioned in the center of the top surface of the tooth. Thus, to ensure that indentations are perpendicular to the top of the tooth 102A and a specified distance from the top surface of the tooth 102A, traditional software packages have allowed an operator to position a "T" bar along a displayed image. In this manner, an operator would position the top portion of the "T" bar along the top edge of the tooth 102A through a combination of moving the stage and rotating the "T" bar. As briefly described above, at 5× magnification the operator has a relatively good idea of the required orientation of the "T" bar, but not enough resolution to position it within 5 microns of the edge. Further, at 50× magnification, locating the top edge of the tooth within 5 microns is possible, but the orientation is difficult because the edge is not straight at this magnification.

What is needed is a technique that more readily allows an operator of an indentation hardness tester to properly position an indenter with respect to a test assembly.

SUMMARY OF THE INVENTION

The present invention is generally directed to an indentation hardness test system that includes a frame having a movable turret, a movable stage for receiving a part, a camera, a display, a processor and a memory subsystem. The turret includes a first objective lens of a microscope and an indenter and the movable stage is configured for receiving a part to be tested. The camera captures images of the part through the microscope, which can then be provided on the display. The processor is electrically coupled to the turret, the movable stage, the camera and the display, as well as the memory subsystem. The memory subsystem stores code that, when executed, instructs the processor to perform a number of steps. That is, the code instructs the processor to capture and store a series of real-time images of the part using the camera. The code also instructs the processor to store stage coordinates, associated with each of the images, and to display a composite image of the part, which includes the series of real-time images assembled according to the associated stage coordinates, on the display.

According to another embodiment of the present invention, the images are stored at a lower resolution than the captured images. According to still another embodiment of the present invention, the code instructs the processor to perform the additional step of displaying a background pattern in the composite image for the portions of the part that have not been captured. According to yet another embodiment of the present invention, the code instructs the processor to perform the additional step of normalizing the series of real-time images when at least one of the images was captured by a second objective lens, with a different focal length than the first objective lens, before displaying the composite image of the part.

In another embodiment, the code instructs the processor to perform the additional step of displaying an outline of the part in a composite image. The step of displaying an outline of the part in the composite image may also include the steps of: examining a frame of an image stream of the part to locate an edge of the part and moving the part in a direction parallel to the edge of the part such that the edge remains in the field of view for a next frame until the outline of the part is complete. The code may also cause the processor to perform the additional steps of overlaying a current position image of the part in the composite image and indicating a location of the current positioned image. Further, the code may allow the processor to perform the additional steps of overlaying an indent position diagram on the composite image and displaying a proposed indent location within an indentation outline that represents a geometry and size (based upon an expected indenter), an expected orientation of the indenter, an expected indenter load and an expected hardness of the part.

These and other features, advantages and objects of the present invention will be further understood and appreciated by those skilled in the art by reference to the following specification, claims and appended drawings.

DETAILED DESCRIPTION OF PREFERRED EMBODIMENTS

A system according to various embodiments of the present invention can be implemented using an indentation hardness tester that includes: a light microscope, a digital camera positioned to collect images through the microscope, an electrically controlled stage capable of moving a test assembly, i.e., an associated part to be tested or a portion of a part mounted in a plastic, in at least two dimensions in a plane perpendicular to the lens of the light microscope, and a processor (or computer system) connected to both the camera and the stage such that the processor can display images acquired by the camera while monitoring and controlling the movements of the stage and its associated part.

Figure 1:
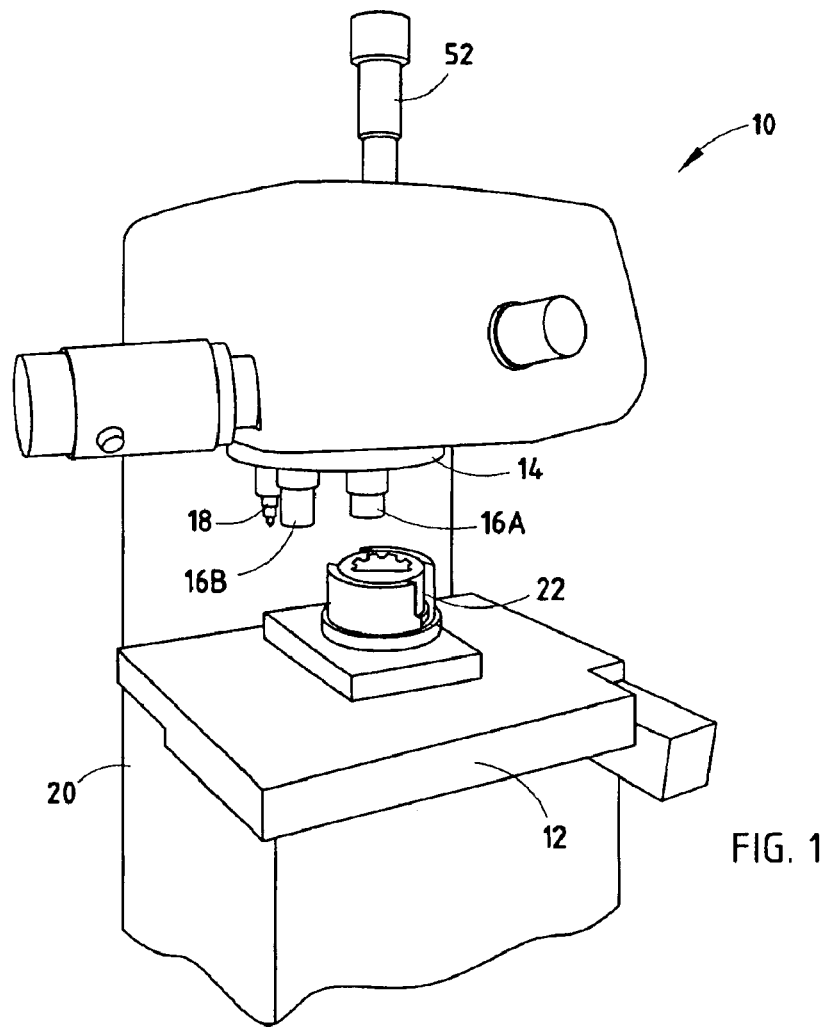
FIG. 1 is a perspective view of an exemplary indentation hardness tester, according to one embodiment of the present invention.

FIG. 1 shows a partial perspective view of an exemplary indentation hardness tester according to one embodiment of the present invention. The indentation hardness test system 10 includes a frame 20 with an attached motorized turret 14, including objective lenses 16A and 16B, which form a portion of a light microscope, and an indenter 18, e.g., a Knoop or Vickers indenter. It should be appreciated that additional objective lenses may be mounted on the turret 14, if desired. A stage 12 is movably attached to the frame 20 such that different areas of a test assembly 22, which is attached to the stage 12, may be inspected.

Figure 1A:
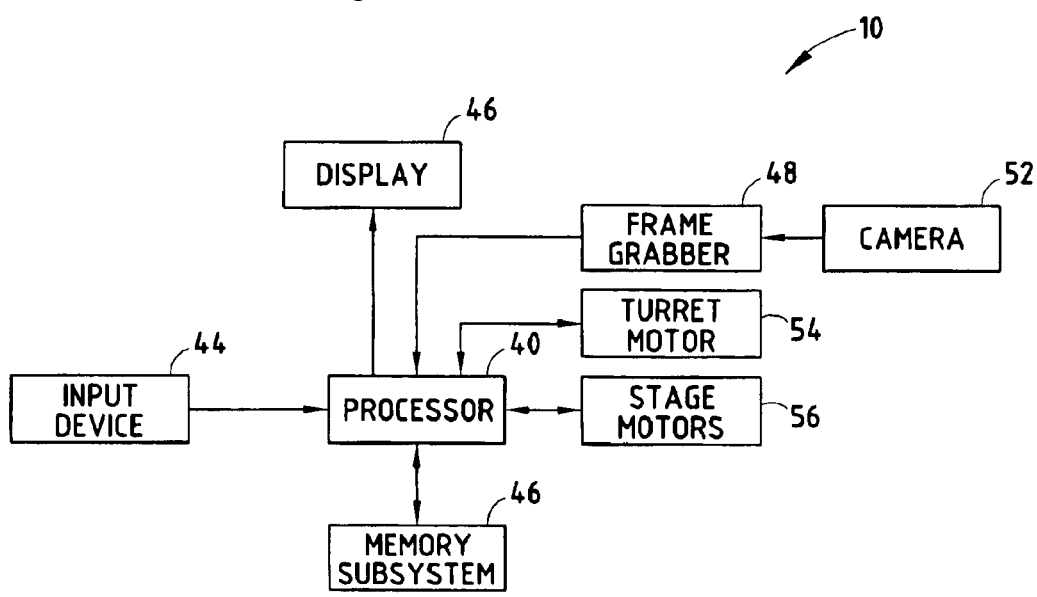
FIG. 1A is an electrical block diagram of an exemplary indentation hardness test system configured according to one embodiment of the present invention.

FIG. 1A depicts an exemplary electrical block diagram of various electrical components that may be included within the definition of the test system 10. As is shown, a processor. 40 is coupled to a memory subsystem 42, an input device 44 (e.g., a joystick, a knob, a mouse and/or a keyboard) and a display 46. A frame grabber 48, which is coupled between the processor 40 and a camera 52, functions to capture frames of digital data provided by the camera 52. The camera 52 may, for example, provide an RS-170 video signal to the frame grabber 48 that is digitized at a rate of 30 Hz. The processor 40 is also coupled to and controls a turret motor 54 to properly and selectively position the objective lenses 16A and 16B and the indenter 18 (e.g., a diamond tipped device), as desired. It should be appreciated that additional indenters may also be located on the turret 14, if desired. The processor 40 is also coupled to stage motors (e.g., three stage motors that move the stage in three dimensions) 56 and provides commands to the stage motors 56 to cause the stage to be moved, in two or three dimensions for image capture and focusing, as desired. The stage motors 56 also provide position coordinates of the stage that are, as is further discussed below, correlated with the images provided by the camera 52. The position coordinates of the stage may be provided by, for example, encoders associated with each of the stage motors 56, and may, for example, be provided to the processor 40 at a rate of about 30 Hz via an RS-232 interface. Alternatively, the processor 40 may communicate with a separate stage controller that also includes its own input device, e.g., a joystick. The processor 40, the memory subsystem 42, the input device 44 and the display 46 may be incorporated within a personal computer (PC). In this case, the frame grabber 48 takes the form of a card that plugs into a motherboard associated with the processor 40. As used herein, the term processor may include a general purpose processor, a microcontroller (i.e., an execution unit with memory, etc., integrated within a single integrated circuit), an application specific integrated circuit (ASIC), a programmable logic device (PLD) or a digital signal processor (DSP).

Figure 2:
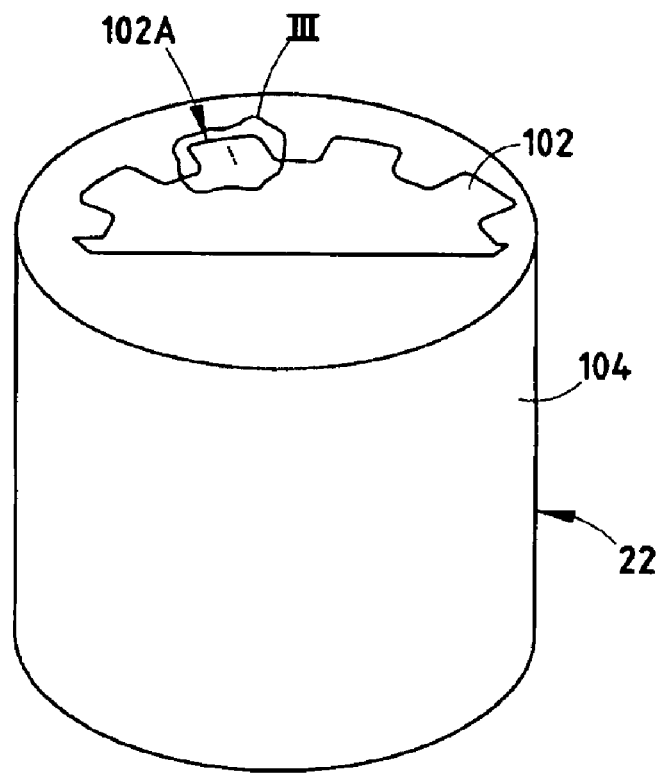
FIG. 2 is a perspective view of a test assembly that includes a portion of a gear mounted in a plastic.
Figure 3:
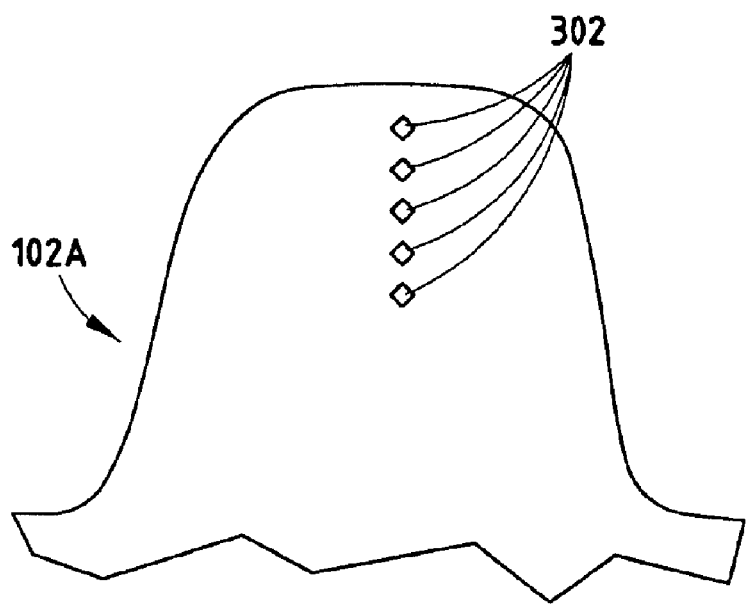
FIG. 3 is an enlarged fragmentary top plan view of a portion of a tooth of the gear of FIG. 2 showing desired indent positions.
Figure 4A:
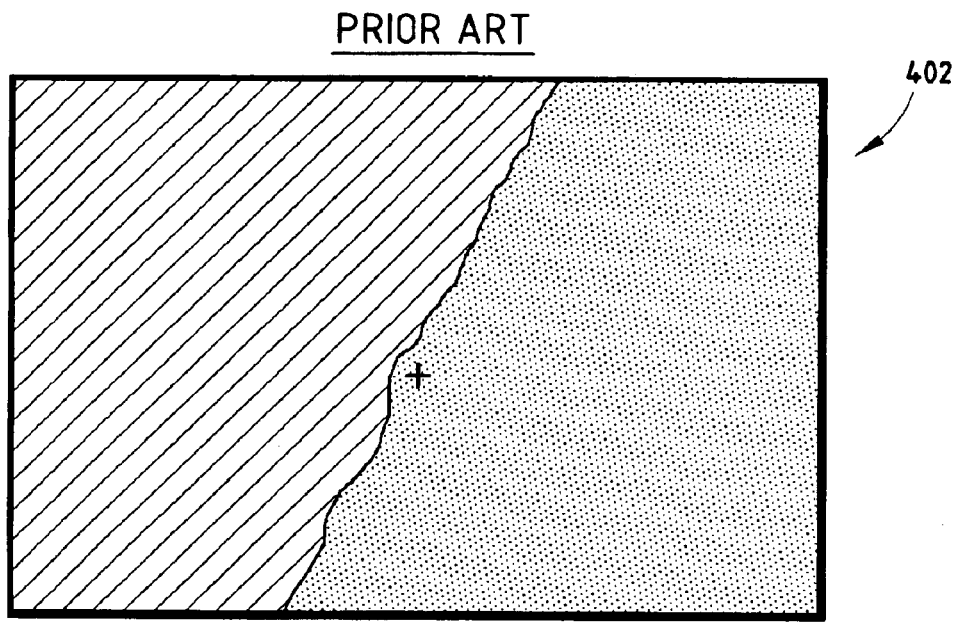
FIG. 4A is a view of a portion of the tooth of the gear of FIG. 2 at 50× magnification, displayed on a monitor of a prior art indentation hardness test system.
Figure 4B:
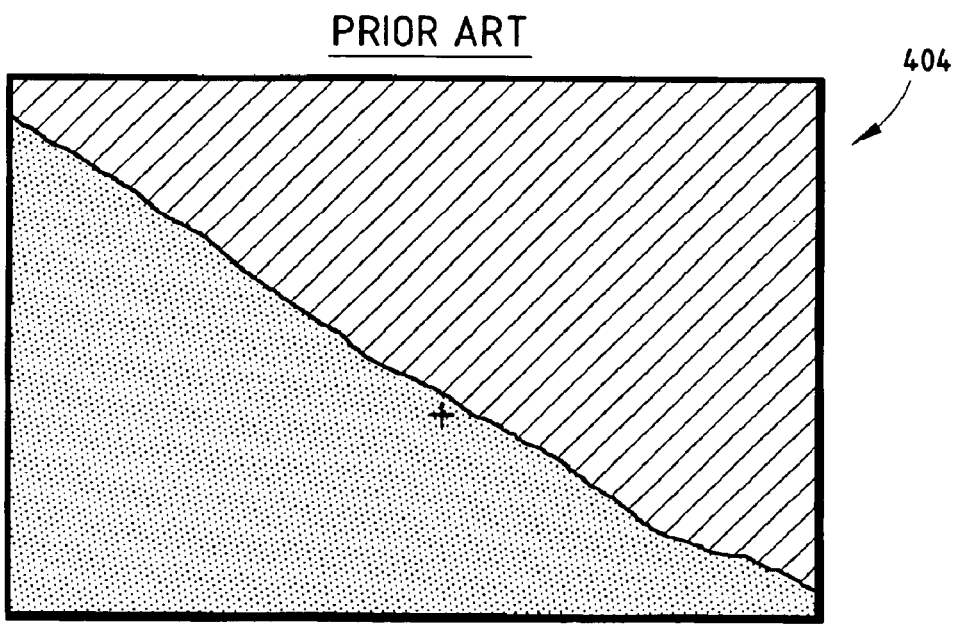
FIG. 4B is a view of a different portion of the tooth of the gear of FIG. 2 at 5× magnification, displayed on a monitor of a prior art indentation hardness test system.
Figure 5:
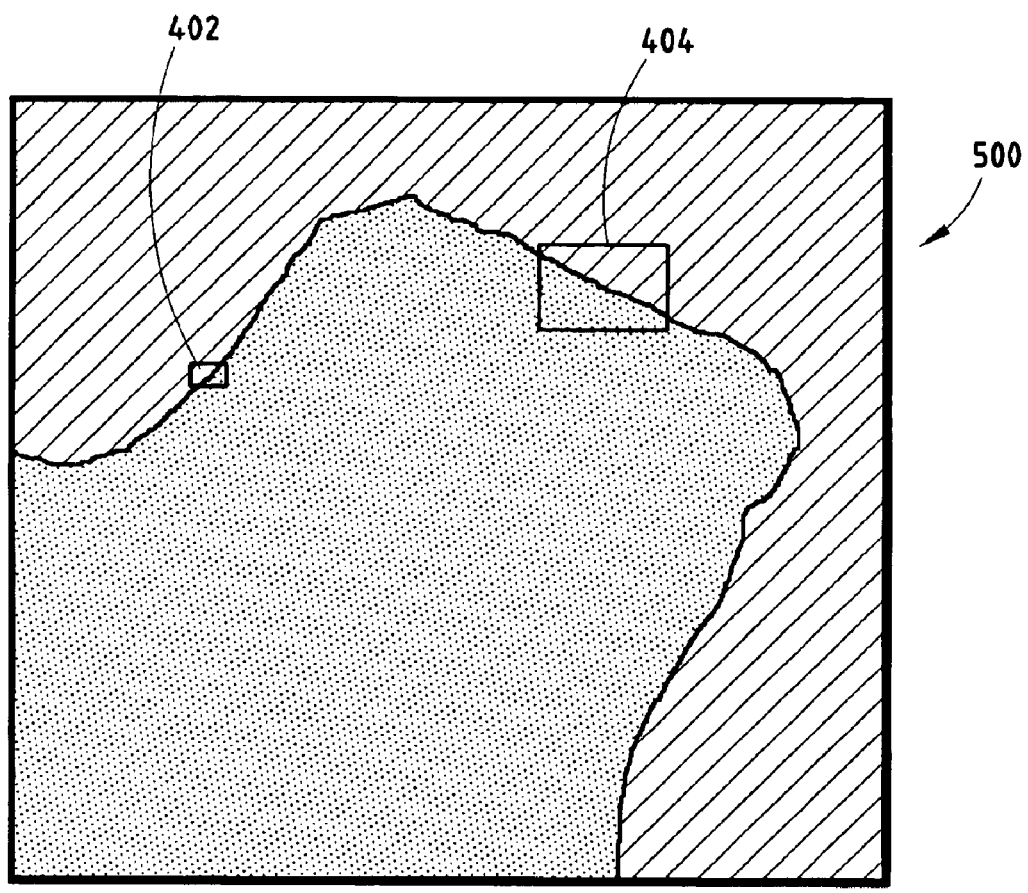
FIG. 5 is a view of a composite image, including the 50× and 5× magnification areas of FIGS. 4A and 4B, respectively, displayed on a monitor of an indentation hardness test system configured according to one embodiment of the present invention.

With reference again to FIG. 2, the test assembly 22 includes a part to be tested, i.e., a portion of a gear 102, that is mounted in the material 104, e.g., a phenolic resin, for testing. With reference to FIG. 3, the tooth 102A of the gear 102 may typically have a face with dimensions of about 0.5 cm by 0.5 cm in which indentations are to be placed in a desired indentation pattern. As is shown in FIG. 3, five evenly spaced indents 302 are depicted. In a typical situation, a part that is to be subjected to indentation hardness testing is often measured in centimeters, while the dimensions of the indentations typically range from 10 to 100 microns. A typical field of view for a light microscope may range from 100 microns to 5000 microns. As previously discussed, and with reference to FIGS. 4B and 4A, respectively, a traditional indentation hardness tester with objective lenses of 5× and 50× allows an operator of the system to see about $\frac{1}{5}^{th}$ of the top portion of a typical tooth at the 5× magnification and only about $\frac{1}{50}^{th}$ of the top surface of the tooth at the 50× magnification. As mentioned above, it is often difficult for the operator to know if the stage is positioned in the center of the face of the tooth when the magnification is set at 50×. According to the present invention and as is shown in FIG. 5, a composite image 500 provides a wider field of view to allow the operator to more precisely determine where the indents are to be positioned on the tooth.

According to one embodiment of the present invention, the processor 40 collects a series of real-time images and stage coordinates as an operator manually traverses the part. In doing so, the processor 40 executes a routine that assembles the data into, i.e., renders, a composite (or panoptic) image that shows the portions of the part that have passed under an objective lens of the microscope, whose objective lens is mounted to the turret of the test system. It should be appreciated that irrespective of the magnification of the image provided, a composite image may be stored at a lower resolution, e.g., a resolution of approximately 5 microns per pixel, if memory limitations are of concern.

Figure 6:
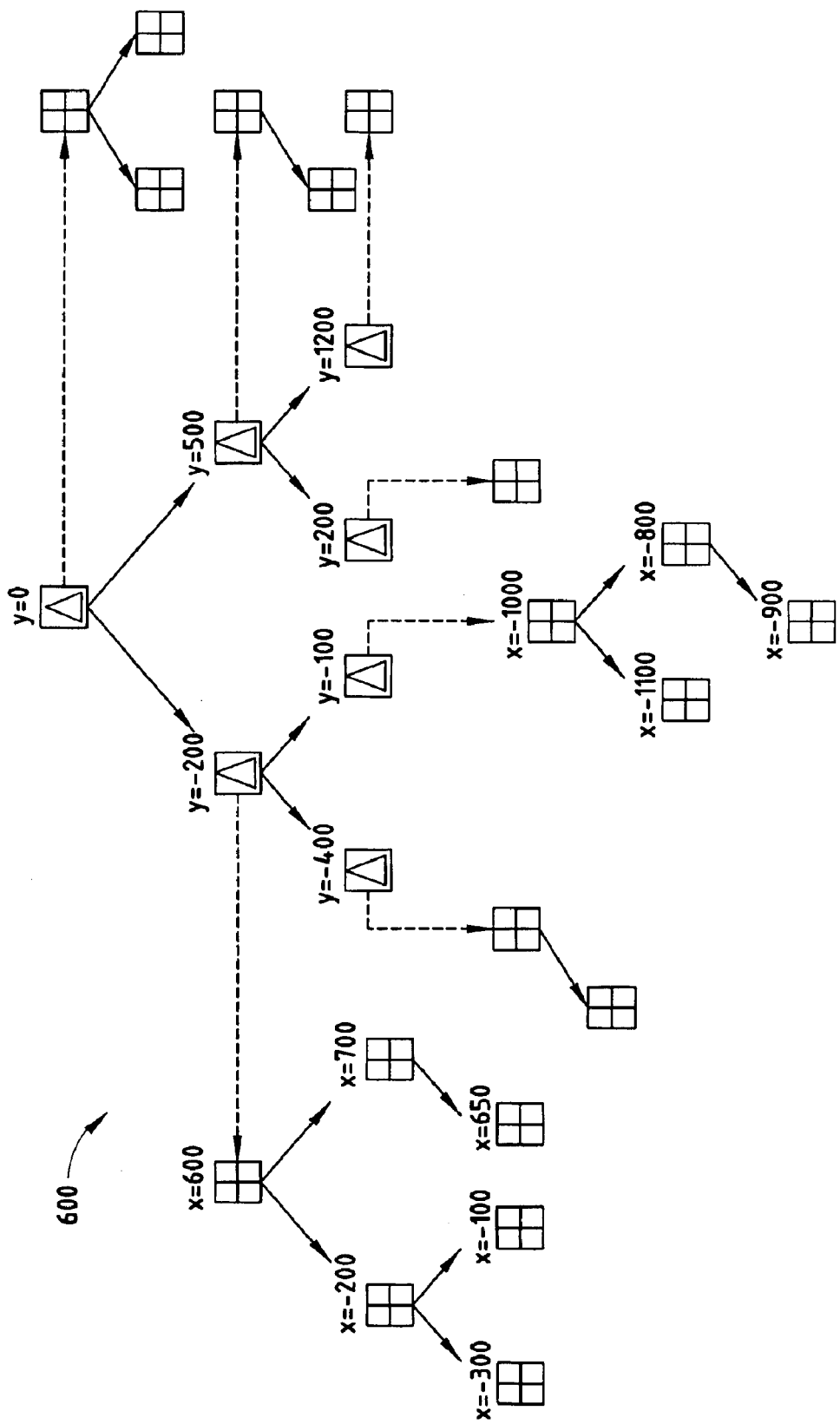
FIG. 6 is an exemplary data structure diagram used to determine individual image locations in a composite image of a part.

With reference to FIG. 6, a data structure diagram 600 is depicted, which is utilized to associate data with a composite image. As can be seen, from review of FIG. 6, the exemplary storage mechanism is based on a tree design. To correlate images from the camera 52, the processor 40 stores images in a time-stamped image queue, e.g., a first-in first-out (FIFO) buffer, and stage positions are recorded in a time-stamped position queue, e.g., another first-in first-out (FIFO) buffer, located in the memory subsystem 46. For each given image in the queue, a routine is implemented that searches for a stage position and velocity information for the period surrounding the time that the image was acquired. Then, using interpolation, the processor 40 accurately determines where the stage 12 was when the image was acquired. This technique allows for accurate positioning of a given image in the composite image. Further, as the direction and velocity of the part is known when a given one of images is taken, Fast Fourier Transform (FFT) techniques, or other image processing techniques, may be utilized to de-blur the image.

Figure 7:
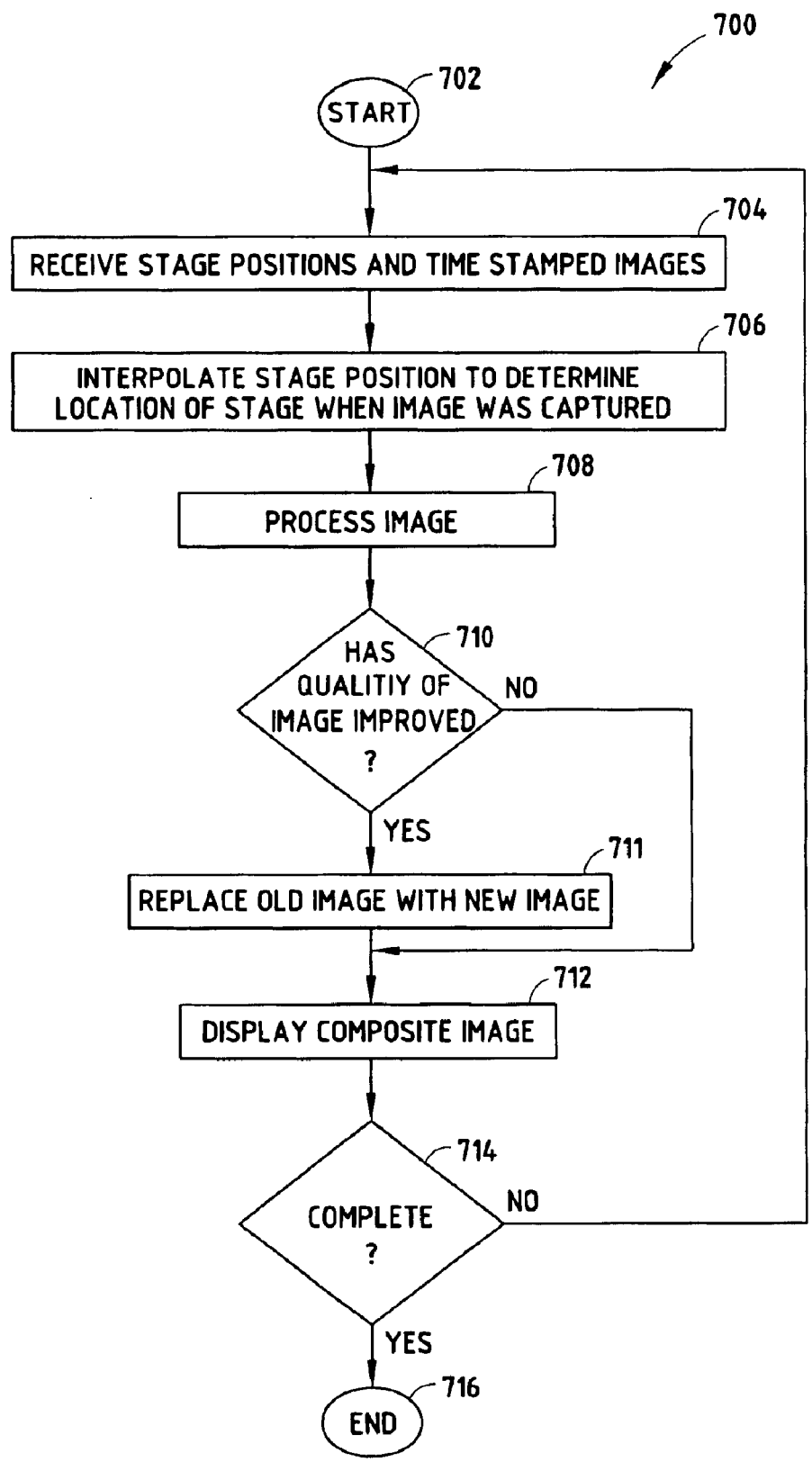
FIG. 7 is a flow chart of a routine for creating a composite image of a part.

With reference to FIG. 7, a routine 700 is depicted that records the quality of the data of a given image, based on the objective lens 16A or 16B selected and the stage 12 velocity. In this manner, new image data only replaces old image data when an operator retraces a portion of the part if the calculated quality is not significantly worse. In step 702, the routine 700 is initiated, at which point control transfers to step 702. Next, in step 704, the processor 40 receives stage positions from the stage motors 56 and time-stamped images from the camera 52, via the frame grabber 48. Next, in step 706, the processor 40 interpolates the stage positions to determine the location of the stage when the image was captured. The acquired images are then processed using various techniques, e.g., de-interlacing, de-blurring, shade correction and stretching/shrinking. After processing the image, in step 708, the processor 40 determines whether the quality (as determined by, for example, stage velocity and a current objective lens) of a particular image has improved in decision step 710. If the quality of the image has improved, control transfers to step 711, where the old image is replaced with a new image. Otherwise, control transfers from step 710 to step 712, where the processor 40 retains the old image and utilizes it in the display of the composite image on the display 46.

A composite image created according to the present invention is well suited for high-speed modification and retrieval while using a minimal amount of computer memory, in comparison to that required for a single large dimension image. This is achieved by storing the composite image in a series of discrete sized two-dimensional tiles, organized in a binary tree by stage position (see FIG. 6). Next, in decision step 714, the processor 40 determines whether the operator has completed the image gathering process. If so, control transfers to step 716, where the routine 700 terminates. Otherwise, control transfers to step 704, where the processor 40 continues to receive and store stage positions and time-stamped images.

According to one embodiment of the present invention, portions of the part that have not been explored are indicated in a contrasting color or pattern, e.g., a lightly shaded non-gray color, with the position of the lens, i.e., a current live view, embedded in the composite image and positioned with respect to its current position on the part. The live view may be indicated by, for example, a thin-lined rectangle overlaid on the composite image. According to another embodiment of the present invention, in order to speed up the capturing of the image of the part, a routine is provided that allows automatic traversal of the contours of the entire part during the image capture process.

According to the present invention, as the operator zooms in on any portion of the composite image, the stage is automatically moved to that location and a live view is embedded in the composite image. In one embodiment, when the objective is set at 50× magnification, the resolution of the live view inside the thin-lined rectangle is about 0.3 microns per pixel and outside of the rectangle the resolution is about 5 microns per pixel. As mentioned above, the system may be advantageously configured such that an operator may manually move the stage with a joystick or other input device. When the system is set up such that a routine is controlling the movement of the stage, the movement of the stage may be indicated in multiple ways. For example, a live view may be fixed, allowing the part to move past the objective lens or, alternatively, the composite image may be fixed and a location of the live view may move.

As previously discussed, traditional indentation hardness test systems have allowed an operator to position a "T" bar along a surface of the part to be tested to ensure that the indentations are perpendicular to the top surface of the gear tooth and at a specified distance from the top surface. However, as previously discussed, at 5× magnification the operator has a relatively good idea of the required orientation of the "T" bar, but not enough resolution to position it within 5 microns of the edge. Further, at 50× magnification, locating the edge within 5 microns is possible but the orientation of the "T" bar is difficult because the edge is not straight at this magnification level. One solution to this problem is to rotate the "T" bar at 5× magnification and position it on the edge at 50× magnification. Another solution that yields a more accurate rotation angle involves allowing the "T" bar to be larger than the field of view for any objective and uses a composite image to accurately position the "T" bar. As previously mentioned, this allows an operator to zoom in on any location of the part and a live view of that portion of the part may be provided at a required resolution.

Traditional indentation hardness test systems have displayed a pattern of desired indents in a separate window. In these systems, an operator has manipulated the indent locations in the pattern window and then instructed the system to make the indents in the part. However, as previously discussed, it is difficult for an operator to correlate the proposed indent locations in a pattern window with the exact position on the part as seen in a live view. Advantageously, embodiments of the present invention allow a pattern window to be overlaid on top of a composite image. Thus, an operator may position indents with respect to large scale features of the part and with respect to the low resolution composite image. In this manner, an operator can then fine tune the indent locations by zooming in and viewing the indent positions through an embedded live view. Further, in a system so configured, screen display area is conserved as only one window is required. That is, multiple windows, each showing a different layer of data, are not required as a composite image of a part may be shown in one window on an indentation test system configured according to the present invention. However, it should be appreciated that an indentation test system configured according to the present invention may implement multiple windows, each showing the composite image and being separately sizeable, zoomable and panable, if desired. According to one embodiment, the present invention allows the conventional "T" bar to be dispensed with and replaced with an improved similar "T" shape, whose top is elongated and can easily be aligned with the part and whose base consists of the proposed indent locations. However, it should be appreciated that shapes, e.g., a line segment and a circle of a known radius, other than the "T" shape may be desirable depending upon the application.

Figure 8A:
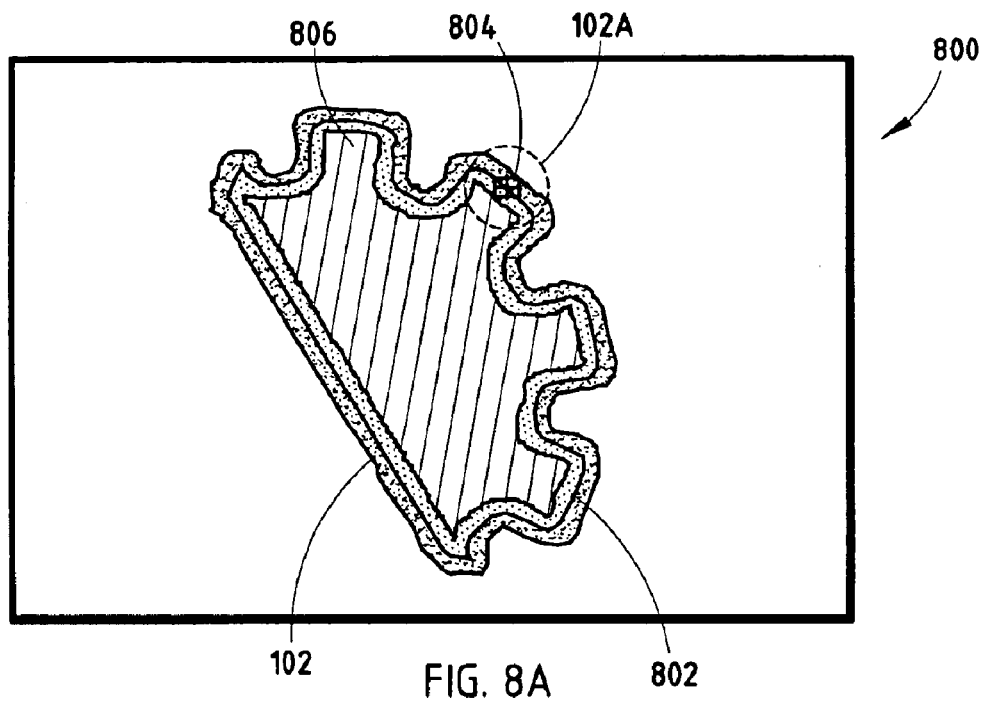
FIGS. 8A–8G are exemplary displays provided by an indentation test system according to one embodiment of the present invention.
Figure 8B:
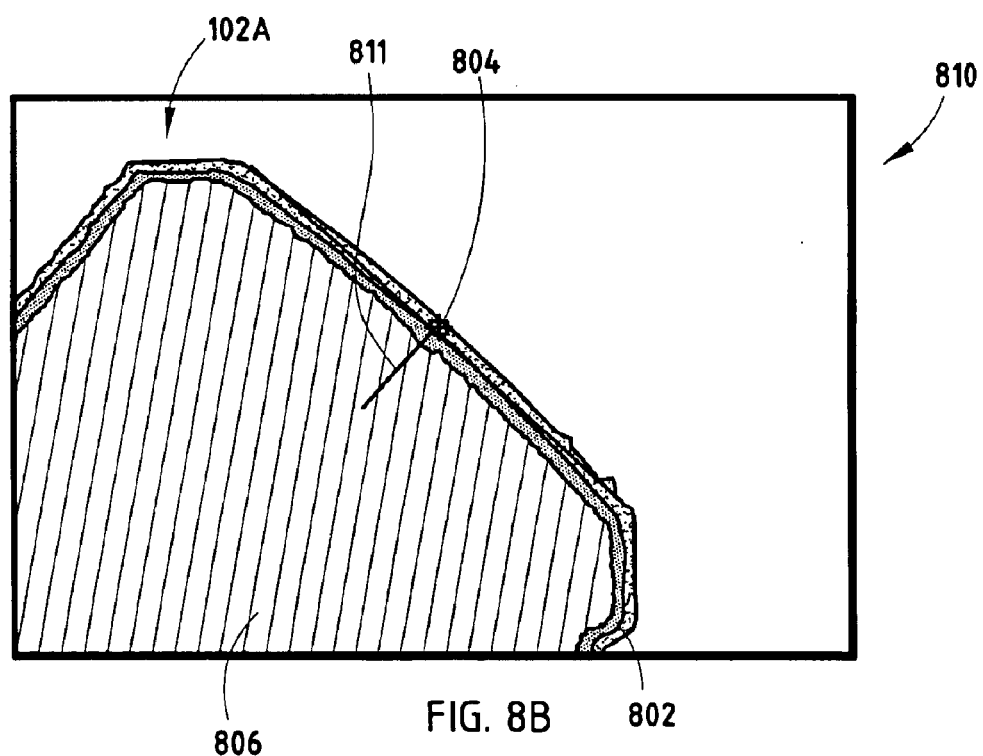
Figure 8C:
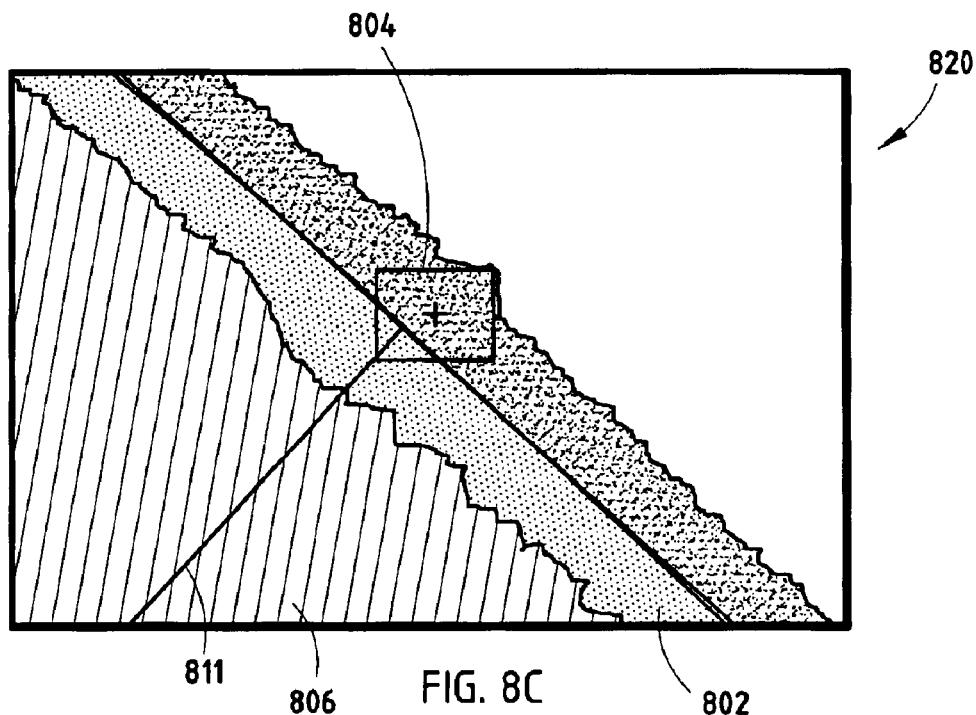
Figure 8D:
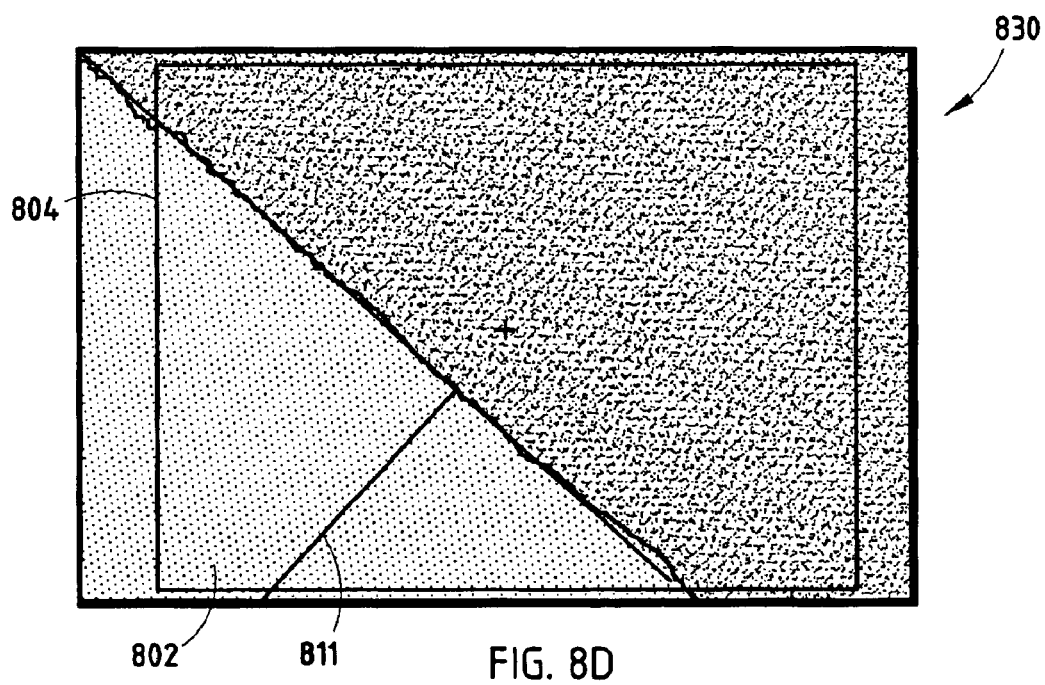
Figure 8E:
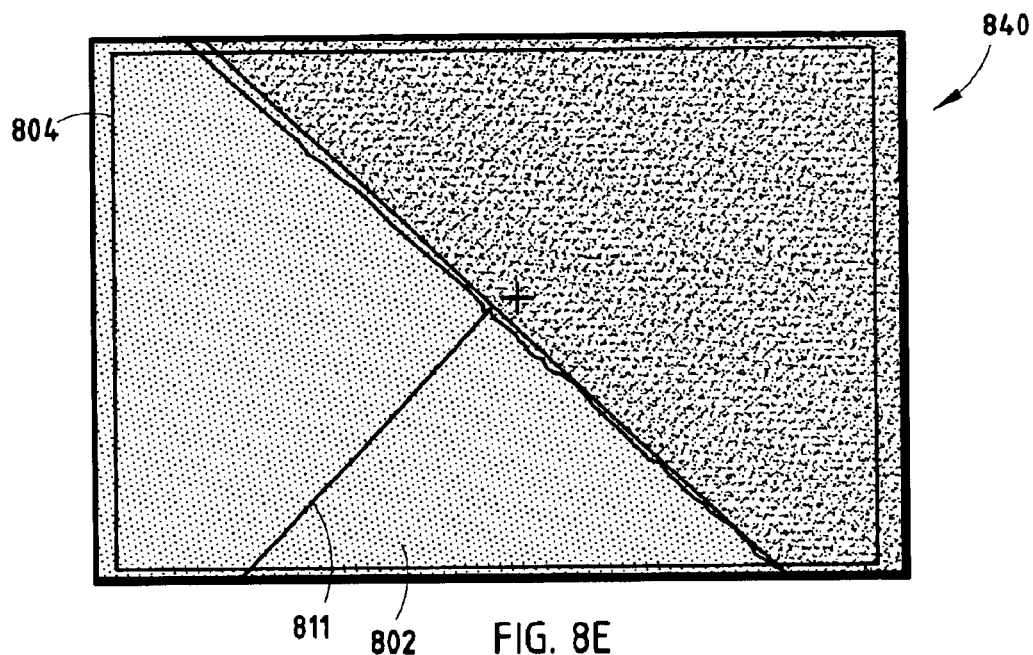
Figure 8F:
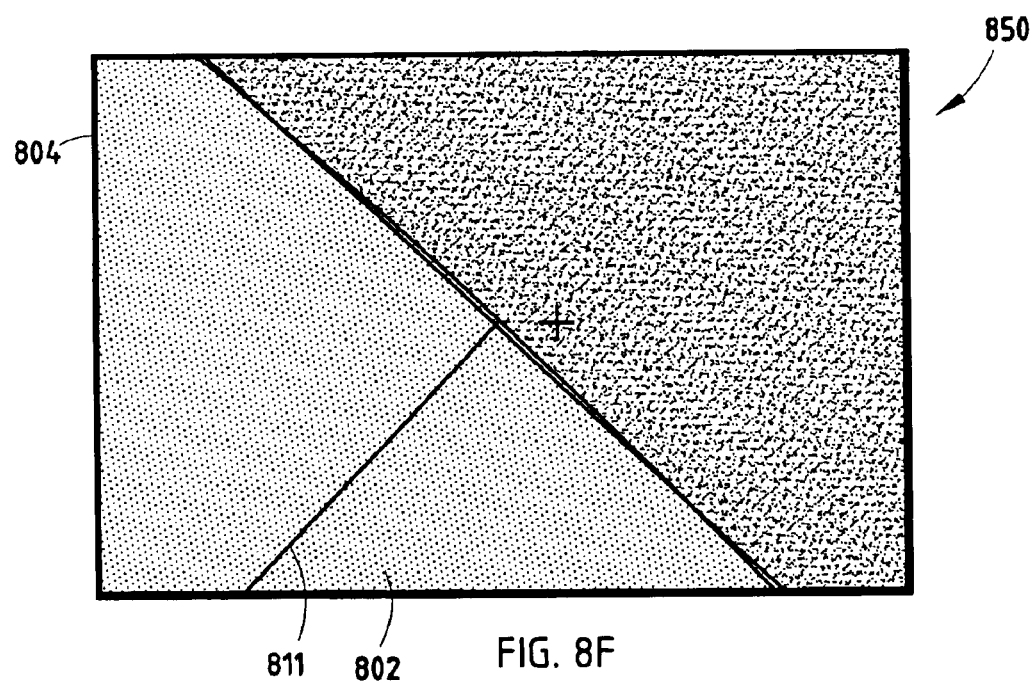
Figure 8G:
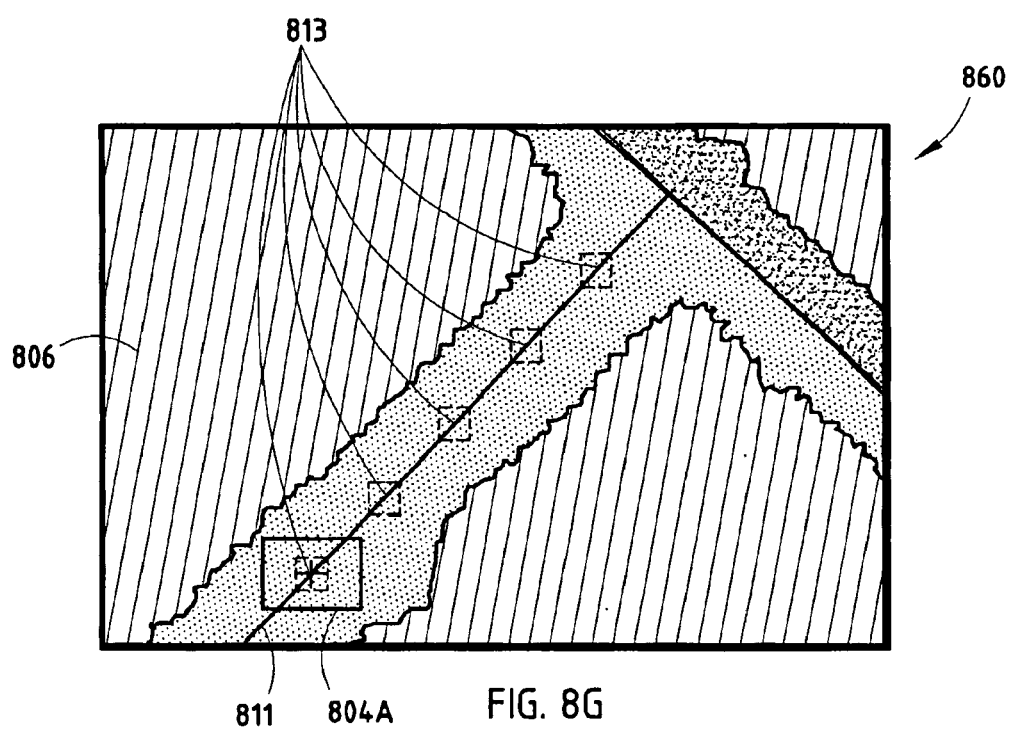

FIG. 8A shows a display 800 of a composite image of the gear 102 after tracing, i.e., capturing images, of an edge 802 of the gear 102. As is shown, the display 800 includes an embedded live image 804 with portion of the gear 102 that has not yet been captured denoted with a background pattern 806. FIG. 8B shows a display 810, which depicts a magnified view of the tooth 102A, which includes the embedded live image 804 and a "T" shape 811 that is used to facilitate the placement of indent locations according to the present invention. FIG. 8C shows a display 820 that is a further magnified view of the composite image of the tooth 102A shown in the display 810, which also includes the live view 804 and the leg of the "T" shape 811 that is utilized for positioning indent locations. FIGS. 8D–8F show displays 830, 840 and 850, respectively, illustrating the alignment of the "T" shape with the tooth 102A in order to facilitate placement of the indent locations. FIG. 8G depicts a display 860 that illustrates the proposed indent locations 813 overlaid on the composite image and a current live image 804A. Embodiments of the present invention advantageously allow the indent locations 813 to be manipulated. That is, the indent locations 813 may be added or removed, moved to a new location and/or rotated/translated as a group, using an appropriated input device, i.e., mouse, keyboard, etc.

Accordingly, a number of techniques have been described herein that advantageously allow an operator of an indentation hardness test system to readily position indent locations in a part that is to be hardness tested.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. An indentation hardness test system, comprising:
   a frame including an attached movable turret, wherein the turret includes a first objective lens that forms a portion of a microscope and an indenter;
   a movable stage for receiving a part attached to the frame;
   a camera for capturing images of the part through the microscope;

a display;

a processor electrically coupled to at least a portion of the turret, the movable stage, the camera and the display; and a memory subsystem coupled to the processor, the memory subsystem storing code that when executed instructs the processor to perform the steps of:

capturing and storing a series of real-time images of the part, wherein the real-time images are provided by the camera;

storing associated stage coordinates for the real-time images, wherein the stage coordinates are provided by the stage; and displaying a composite image of the part, wherein the composite image includes the series of real-time images assembled according to the associated stage coordinates.

2. The system of claim 1, wherein the series of real-time images are stored at a lower resolution than the captured images.

3. The system of claim 1, wherein the code instructs the processor to perform the additional step of:

displaying a background pattern in the composite image for portions of the part that have not been captured.

4. The system of claim 1, wherein the code instructs the processor to perform the additional step of:

normalizing the series of real-time images when at least one of the real-time images was captured by a second objective lens with a different focal length than the first objective lens before displaying the composite image of the part.

5. The system of claim 1, wherein the code instructs the processor to perform the additional step of:

displaying an outline of the part in the composite image.

6. The system of claim 5, wherein the step of displaying an outline of the part in the composite image includes the steps of:

examining a frame of an image stream of the part to locate an edge of the part; and moving the part in a direction parallel to the edge of the part such that the edge remains in the field of view for a next frame until the outline of the part is complete.

7. The system of claim 1, wherein the code instructs the processor to perform the additional steps of:

overlaying a current position image of the part in the composite image; and indicating a location of the current position image.

8. The system of claim 1, wherein the code instructs the processor to perform the additional steps of:

overlaying an indent position diagram on the composite image; and displaying a proposed indent location with an indentation outline that represents a geometry and size based upon an expected indenter, an expected orientation of the indenter, an expected indenter load and an expected hardness of the part.

9. An indentation hardness test system, comprising:

a frame including an attached movable turret, wherein the turret includes a first objective lens that forms a portion of a microscope and an indenter;

a movable stage for receiving a part attached to the frame;

a camera for capturing images of the part through the microscope;

a display;

a processor electrically coupled to at least a portion of the turret, the movable stage, the camera and the display; and a memory subsystem coupled to the processor, the memory subsystem storing code that when executed instructs the processor to perform the steps of:

capturing and storing a series of real-time images of the part, wherein the real-time images are provided by the camera;

storing associated stage coordinates for the real-time images, wherein the stage coordinates are provided by the stage; and displaying a composite image of the part, wherein the composite image includes the series of real-time images assembled according to the associated stage coordinates, and wherein the composite image includes a background pattern for portions of the part that have not been captured.

10. The system of claim 9, wherein the series of real-time images are stored at a lower resolution than the captured images.

11. The system of claim 9, wherein the code instructs the processor to perform the additional step of:

normalizing the series of real-time images when at least one of the real-time images was captured by a second objective lens with a different focal length than the first objective lens before displaying the composite image of the part.

12. The system of claim 9, wherein the code instructs the processor to perform the additional step of:

displaying an outline of the part in the composite image.

13. The system of claim 12, wherein the step of displaying an outline of the part in the composite image includes the steps of:

examining a frame of an image stream of the part to locate an edge of the part; and moving the part in a direction parallel to the edge of the part such that the edge remains in the field of view for a next frame until the outline of the part is complete.

14. The system of claim 9, wherein the code instructs the processor to perform the additional steps of:

overlaying a current position image of the part in the composite image; and indicating a location of the current position image.

15. The system of claim 9, wherein the code instructs the processor to perform the additional steps of:

overlaying an indent position diagram on the composite image; and displaying a proposed indent location with an indentation outline that represents a geometry and size based upon an expected indenter, an expected orientation of the indenter, an expected indenter load and an expected hardness of the part.

16. An indentation hardness test system, comprising:

a frame including an attached movable turret, wherein the turret includes a first objective lens that forms a portion of a microscope and an indenter;

a movable stage for receiving a part attached to the frame;

a camera for capturing images of the part through the microscope;

a display;

a processor electrically coupled to at least a portion of the turret, the movable stage, the camera and the display; and a memory subsystem coupled to the processor, the memory subsystem storing code that when executed instructs the processor to perform the steps of:

capturing and storing a series of real-time images of the part, wherein the real-time images are provided by the camera;

storing associated stage coordinates for the real-time images, wherein the stage coordinates are provided by the stage;

displaying a composite image of the part, wherein the composite image includes the series of real-time images assembled according to the associated stage coordinates, and wherein the composite image includes a background pattern for portions of the part that have not been captured;

overlaying a current position image of the part in the composite image; and indicating a location of the current position image.

17. The system of claim 16, wherein the series of real-time images are stored at a lower resolution than the captured images.

18. The system of claim 16, wherein the code instructs the processor to perform the additional step of:

normalizing the series of real-time images when at least one of images was captured by a second objective lens with a different focal length than the first objective lens before displaying the composite image of the part.

19. The system of claim 16, wherein the code instructs the processor to perform the additional step of:

displaying an outline of the part in the composite image.

20. The system of claim 19, wherein the step of displaying an outline of the part in the composite image includes the steps of:

examining a frame of an image stream of the part to locate an edge of the part; and moving the part in a direction parallel to the edge of the part such that the edge remains in the field of view for a next frame until the outline of the part is complete.

21. The system of claim 16, wherein the code instructs the processor to perform the additional steps of:

overlaying an indent position diagram on the composite image; and displaying a proposed indent location with an indentation outline that represents a geometry and size based upon an expected indenter, an expected orientation of the indenter, an expected indenter load and an expected hardness of the part.

22. A method for providing a composite image of a part, comprising the steps of:

capturing and storing a series of real-time images of a part, wherein the real-time images are provided by a camera;

storing associated stage coordinates for the series of real-time images, wherein the stage coordinates are provided by a stage, and wherein the part is attached to the stage;

displaying a composite image of the part, wherein the composite image includes the series of real-time images assembled according to the associated stage coordinates;

overlaying a current position image of the part in the composite image; and indicating a location of the current position image.

23. The method of claim 22, further including the step of:

displaying a plurality of manipulatable indent locations on the composite image.

* * * * *